United States Patent [19]

Waller

[11] Patent Number: 5,214,200

[45] Date of Patent: May 25, 1993

[54] PROCESS FOR PRODUCING ORGANIC ESTERS BY REACTING A CARBOXYLIC ACID AND A DIALKYL ETHER

[75] Inventor: Francis J. Waller, Allentown, Pa.

[73] Assignee: Air Products and Chemicals, Inc., Allentown, Pa.

[21] Appl. No.: 869,606

[22] Filed: Apr. 15, 1992

[51] Int. Cl.$^5$ .............................................. C07C 67/24
[52] U.S. Cl. .................................................. 560/240
[58] Field of Search ........................................ 560/240

[56] References Cited

U.S. PATENT DOCUMENTS 2,030,835 2/1936 Cox ...................................... 560/240
3,510,511 5/1970 Conseiller et al. .................. 260/496

OTHER PUBLICATIONS

Derevitskaya & Coworkers, Tetrahedron Letters, 49 (1970) 4269.

*Primary Examiner*—Michael L. Shippen
*Attorney, Agent, or Firm*—Keith D. Gourley; James C. Simmons; William F. Marsh

[57] ABSTRACT

The present invention is a process for producing organic esters wherein a dialkyl ether and a carboxylic acid are reacted in the presence of a catalyst consisting essentially of an iodide of a Group IA element under reaction conditions sufficient to form a reaction mixture comprising the desired organic ester and an alcohol and recovering the ester from the reaction product mixture. For example, methyl acetate can be prepared by reacting dimethyl ether and acetic acid in the presence of a hydrogen iodide or lithium iodide catalyst under conditions sufficient to form methyl acetate and methanol. While typical processes produce an azeotropic mixture of the desired organic ester and water, the claimed process utilizes a combination or reactants and catalysts wherein water is not produced in appreciable amounts. Therefore, the organic ester product can be separated conveniently thereby avoiding a cumbersome azeotropic distillation step as required in prior art processes.

17 Claims, No Drawings

PROCESS FOR PRODUCING ORGANIC ESTERS BY REACTING A CARBOXYLIC ACID AND A DIALKYL ETHER

TECHNICAL FIELD OF THE INVENTION

The present invention is a process for producing organic esters wherein a dialkyl ether and a carboxylic acid are reacted in the presence of a catalyst consisting essentially of an iodide of a Group IA element under reaction conditions sufficient to form the desired organic ester. Organic esters are used in numerous applications such as solvents in coating compositions and as plasticizers.

BACKGROUND OF THE INVENTION

Organic esters, represented by the generic formula, $RCO_2R'$ wherein R and R' are independently selected from an organic functionality, are utilized in numerous applications. Recent data indicate that more than 600 esters are currently sold in the United States and more than 100 esters are available in medium and bulk lots. On the basis of bulk production, poly(ethylene terephthalate) is prepared in greatest quantity and is used in manufacturing polyester fibers and thermosetting fibers. Poly(ethylene terephthalate) is typically prepared by reacting terephthalic acid and ethylene glycol or by transesterification of dimethyl terephthalate with ethylene glycol.

Numerous catalytic processes are known for producing organic esters including reacting an alcohol and either an acid anhydride, an acid chloride, an amide or a nitrile in the presence of a suitable catalyst under reaction conditions sufficient to form the desired product. For example, organic esters can be prepared by reacting a carboxylic acid and an alcohol in the presence of catalysts such as strong mineral acids, tin salts, organo-titanates, silica gel and cation-exchange resins. Unfortunately, these reactions proceed via a reversible equilibrium and can be driven toward completion only by removing the desired ester product or water.

Highly volatile organic esters such as methyl formate, methyl acetate and ethyl formate, typically have lower boiling points than their corresponding alcohols and can be readily removed from the product mixture by conventional methods. However, water cannot be easily separated by simple distillation from aliphatic alcohols and esters of medium volatility because the product mixture forms an azeotrope. Consequently, processes for making such esters are highly energy intensive because the water/ester azeotrope must be broken in order to recover the desired ester.

U.S. Pat. No. 3,510,511 discloses a process for preparing an ester by reacting a carboxylic acid and an alkyl ether. The process comprises continuously introducing an ether of an alkanol and a carboxylic acid simultaneously in a proportion to two moles acid to one mole ether, into a boiling mixture initially consisting of sulfuric acid and the ether in a proportion of 0.7 to 1.3 mol of sulfuric acid per mol of ether; continuously extracting the vapors evolved from the reaction mixture and isolating the ether product from water via fractional distillation.

Derevitskaya and coworkers, Tetrahedron Letters, 49 (1970) 4269 disclose a process for preparing alkyl esters by reacting an alkyl tert-butyl ether and a carboxylic acid in the presence of a catalytic amount of a proton-donating agent such as sulfuric acid or para-toluenesulfonic acid. The reaction is represented by the formula:

$$R\text{—}O\text{—tert—}C_4H_9 + R'\text{—}CO_2H \rightarrow R'\text{—}CO_2R + CH_2\!=\!C(CH_3)_2 + H_2O.$$

The driving force of the above-mentioned reaction results from evolution of isobutylene. The desired organic ester is separated from the reaction mixture by diluting the mixture with diethyl ether, washing with aqueous sodium hydrogen carbonate and water and drying over sodium sulfate or magnesium sulfate. Following removal of diethyl ether, the residue is distilled to yield the desired ester.

Considerable research is being conducted in order to develop a process for preparing organic esters which eliminates the shortcomings of the above-mentioned prior art processes. Those skilled in the art of producing organic esters are particularly interested in commercial processes wherein water is not produced in appreciable amounts during the reaction.

BRIEF SUMMARY OF THE INVENTION

The present invention is a process for producing organic esters which comprises reacting a carboxylic acid and a dialkyl ether in the presence of a catalyst consisting essentially of an iodide of a Group IA element under conditions sufficient to form the organic ester and recovering the organic ester. The instant process utilizes a new class of catalysts which is capable of producing a product mixture which is substantially free of water thereby overcoming numerous problems associated with prior art processes wherein the desired organic ester must be separated from the unwanted water via fractional distillation.

Dialkyl ethers suitable for practicing the invention are represented by the formula R—O—R' wherein R is a primary, secondary or tertiary alkyl having from 1 to about 10 carbon atoms and R' is a primary, secondary or tertiary alkyl having from 1 to about 7 carbon atoms or a linear or branched alkoxy alkyl having from 2 to about 7 carbon atoms. Suitable carboxylic acids are represented by the formula $R''CO_2H$ wherein R'' is an alkyl, aryl or alkyl aryl having from 1 to about 22 carbon atoms.

The claimed process can be carried out in a batch reactor or a continuous flow reactor under a broad range of reaction conditions including temperatures ranging from 100° to about 400° C. and pressures ranging from 1 atmosphere to about 150 atmospheres.

DETAILED DESCRIPTION OF THE INVENTION

The present invention is a process for producing organic esters which utilizes a new class of catalysts capable of producing a product mixture which is substantially free of water thereby overcoming problems associated with prior art processes wherein the desired organic ester must be separated from water via fractional distillation. Moreover, the present process simplifies prior art processes for producing organic esters by eliminating the necessity for tedious washing steps with basic solutions to remove residual acid catalyst from the reaction product.

Applicants' process for producing organic esters comprises reacting a carboxylic acid and a dialkyl ether in the presence of a catalyst consisting essentially of an iodide of a Group IA element under conditions sufficient to form the desired organic ester and recovering the organic ester. Reaction conditions suitable for practicing the present invention will vary depending upon the particular carboxylic acid and dialkyl ether utilized to form the organic ester. The process can be conducted at a temperature ranging from about 100° to about 400° C. and a pressure ranging from 1 atmosphere to about 150 atmospheres. Typically, the molar ratio of carboxylic acid to dialkyl ether ranges from 1:1 to 40:1 and preferably ranges from 3:1 to 25:1.

Typical reaction times vary depending on the chosen reaction conditions and the choice of reactants. However, suitable reaction times range from 5 minutes to 5 hours and can be easily deduced by those of ordinary skill in the art. Likewise, one of ordinary skill in the art can readily choose the carboxylic acid and dialkyl ether required to produce the organic ester to be prepared. Suitable reaction conditions can be readily determined without undue experimentation by one of organic skill in the art to which this invention pertains.

Dialkyl ethers suitable for use as reactants in the present process are represented by the formula R—O—R' wherein R is a primary, secondary or tertiary alkyl having from 1 to about 10 carbon atoms and R' is a primary, secondary or tertiary alkyl having from 1 to about 7 carbon atoms or a linear or branched alkoxy alkyl having from 2 to about 7 carbon atoms. In a preferred embodiment, the dialkyl ether is chosen such that when R is a tertiary alkyl, then R' is not a secondary of tertiary alkyl in order to reduce the amount of elimination products formed during the process.

Carboxylic acids suitable for use as reactants in the present process are represented by the formula R''CO$_2$H wherein R'' is an alkyl, aryl or alkyl aryl having from 1 to about 22 carbon atoms. Preferably, the carboxylic acid is a linear or branched alkyl having from 1 to about 22 carbon atoms, and most preferably, a linear alkyl having from 1 to about 10 carbon atoms. A mixture of dialkyl ethers and/or carboxylic acids can be used in the present process to produce a mixture or organic esters.

The catalysts according to the present process consist essentially of an iodide of a Group IA element or a mixture or two or more iodides of Group IA elements. Preferred catalysts include HI and LiI. Suitable solvents for practicing the present process include any solvent or mixture of solvents wherein the solvent is inert with respect to the reactants under the enumerated process conditions. The term, inert, means that the solvent will not react with the carboxylic acid or dialkyl ether under the chosen reaction conditions. Choice of solvent is not critical to the practice of the present invention. Suitable solvents include hydrocarbons such as toluene, xylene and the like.

Those skilled in the art will recognize that the reactants and/or organic ester product may serve as a reaction medium in certain cases thereby eliminating the necessity of introducing an inert solvent. The process of the present invention can be operated either in a batch mode in the liquid phase or as a continuous process. In carrying out the present invention on a commercial scale, the process is preferably operated in a continuous mode. Suitable reactors can be constructed of any suitable corrosion-resistant material.

Essentially quantitative conversion of the dialkyl ether to the organic ester can be achieved when the process of this invention is run in a continuous mode wherein the desired organic ester is removed immediately following its formation via distillation. Prompt removal of the organic ester from the reaction product mixture minimizes further reaction of the ester with the catalyst to yield the corresponding carboxylic acid or carboxylic salt, and organic iodide.

In a preferred embodiment of the present invention, methyl acetate can be formed by reacting dimethyl ether and acetic acid in the presence of a catalyst consisting essentially of an iodide of a Group IA element under conditions sufficient to form methyl acetate and recovering the methyl acetate from the reaction mixture. Suitable reaction conditions range from about 125° to about 250° C. and a pressure ranging from 1 atmosphere to about 150 atmospheres. Consistent with the general embodiment of this invention, the process for producing methyl acetate can be carried out in a batch reactor or a continuous flow reactor.

When a continuous flow reactor is utilized, essentially quantitative conversion from dimethyl ether to methyl acetate is accomplished when methyl acetate is continuously removed from the product mixture by distillation. Continuous removal of methyl acetate from the reaction mixture essentially eliminates the undesirable side reaction between methyl acetate and the iodide catalyst. Typically, the molar ratio of acetic acid to dimethyl ether ranges from 1:1 to 40:1 and preferably, between 3:1 and 25:1.

The following examples are given to illustrate the process of the present invention and should not be construed as limiting the scope.

EXPERIMENTAL SECTION

The reaction products were analyzed by DB-1701 FSOT capillary column interfaced to a flame ionization detector. Quantitation was obtained using an internal standard technique. All organic compounds were verified by gas chromatography/mass spectrometry (GC/MS). The lower limit of detection for the components of interest was approximately 0.002 wt. %. The reactions were conducted in a 300 cc Hastelloy C autoclave, equipped with a dip tube for loading dimethyl ether from a preweighed cylinder. The autoclave was further equipped with a thermocouple, cooling coils, a belt driven magnetic stirrer and an inlet for gases. In addition the autoclave was protected from overpressure by a rupture disk and a relief valve. All inlet lines, valves and other surfaces being exposed to methyl iodide were made of either Hastelloy C or Inconel.

The following general procedure was used to load, pressurize, run and unload the autoclave. The autoclave was charged with acetic acid, the enumerated iodide catalyst or other components mentioned in the Table. The autoclave was sealed, pressurized with nitrogen to test for leaks, vented, pressurized with CO, syn-gas or N$_2$ at least thrice, and vented to approximately 20 psi. Dimethyl ether was transferred to the autoclave from a preweighed cylinder. While stirring, CO, syn-gas or N$_2$ pressure was increased to 300–400 psi and then the temperature brought up to operating temperature. At operating temperature, the pressure was increased to operating pressure. The reaction was run for the desired length of time maintaining the autoclave at constant pressure. After the reaction was complete, the autoclave was cooled to room temperature, depressurized and the contents were poured from the reactor. The reactor was rinsed with 25 ml acetic acid or toluene and combined with the reactor discharge.

Runs 1 through 9 in the TABLE illustrate the process of the present invention wherein acetic acid and dimethyl ether are reacted in the absence of a catalyst, in the presence of a catalyst consisting essentially of an iodide of a Group IA element and in the presence of lithium acetate. The reactions were run at a temperature of 175° C. under the enumerated atmospheres. Runs 1 and 2, conducted in the absence of a catalyst, demonstrate that essentially no methyl acetate (MA) is formed under the enumerated reaction conditions and that the presence of a CO atmosphere provides only a minor effect upon the formation of methyl acetate. Runs 3 through 6 demonstrate that dimethyl ether is converted to methyl acetate in the presence of LiI under an atmosphere of either CO, $N_2$ or $CO/H_2$. Runs 6 and 7 demonstrate that similar product distributions were obtained with either HI or LiI when the atmosphere was 50% CO in $H_2$. Under the reaction conditions according to Runs 1 through 9, dimethyl ether did not directly react with CO to give methyl acetate and LiOAc was essentially ineffective in producing methyl acetate, especially when compared with LiI.

TABLE

REACTION OF ACETIC ACID AND DIMETHYL ETHER WITH GROUP IA IODIDE CATALYSTS

| Run | Charged* DME (mmol) | Atmosphere (psig) | Catalyst (mmol) | Product Distribution MA (mmol) | $Ac_2O$ | MeI | Rxn. Time (min.) |
|---|---|---|---|---|---|---|---|
| 1 | 130 | $N_2$,1500 | None | — | — | — | 75 |
| 2 | 120 | CO,1500 | None | 1.6 | — | 0.1 | 75 |
| 3 | 102 | $N_2$,1500 | LiI(14.9) | 16.5 | — | 8.2 | 75 |
| 4 | 122 | CO,1500 | LiI(7.5) | 12.9 | 0.1 | 7.1 | 45 |
| 5 | 226 | $N_2$,1500 | LiI(14.9) | 25.6 | — | 11.6 | 75 |
| 6 | 122 | $CO/H_2$,1500 | LiI(14.9) | 20.4 | — | 10.4 | 45 |
| 7 | 109 | $CO/H_2$,1500 | HI(16.0) | 15.4 | — | 13.4 | 45 |
| 8 | 122 | $N_2$,1500 | LiOAc(11.4) | 0.6 | — | — | 75 |
| 9 | 128 | $CO/H_2$,1500 | LiOAc(22.7) | 0.4 | — | 0.1 | 45 |

*2.35–2.45 mol acetic acid
MA: Methyl acetate
$Ac_2O$: Acetic anhydride
MeI: Methyl iodide While the embodiments of the present process have been disclosed with reference to specific examples, one of ordinary skill can make various changes and modifications to the invention to adapt it to various uses and conditions. As such, these changes and modifications are properly, equitably, and intended to be, within the full range of equivalents of the following claims.

Having thus described the present invention, what is now deemed appropriate for Letters Patent is set forth in the following Claims.

I claim:

1. A process for producing an organic ester comprising reacting a carboxylic acid and a dialkyl ether in the presence of a catalyst consisting essentially of an iodide of a Group IA element under conditions sufficient to form the ester and recovering the ester.

2. The process according to claim 1 wherein the reaction is conducted at a temperature ranging from 100° to about 400° C. and a pressure ranging from 1 atmosphere to about 150 atmospheres.

3. The process according to claim 2 wherein the dialkyl ether is represented by the formula R—O—R' wherein R is a primary, secondary or tertiary alkyl having from 1 to about 10 carbon atoms and R' is a primary, secondary or tertiary alkyl having from 1 to about 7 carbon atoms or a linear or branched alkoxy alkyl having from 2 to about 7 carbon atoms.

4. The process according to claim 3 wherein the carboxylic acid is represented by the formula R"$CO_2$H wherein R" is an alkyl, aryl or alkyl aryl having from 1 to about 22 carbon atoms.

5. The process according to claim 4 wherein the reaction is carried out in a batch reactor or a continuous flow reactor.

6. The process according to claim 5 wherein the reaction is carried out in the liquid phase.

7. A process for producing an organic ester comprising reacting a carboxylic acid and a dialkyl ether in the presence of a catalyst comprising an iodide selected from the group consisting of HI and LiI under conditions sufficient to form the organic ester and recovering the organic ester.

8. The process according to claim 7 wherein the dialkyl ether is represented by the formula R—O—R' wherein R is a primary, secondary or tertiary alkyl having from 1 to about 10 carbon atoms and R' is a primary, secondary or tertiary alkyl having from 1 to about 7 carbon atoms or a linear or branched alkoxy alkyl having from 2 to about 7 carbon atoms with the proviso that when R is a tertiary alkyl then R' is not a secondary of tertiary alkyl.

9. The process according to claim 8 wherein the reaction is conducted at a temperature ranging from 100° to about 400° C. and a pressure ranging from 1 atmosphere to about 150 atmospheres.

10. The process according to claim 9 wherein the carboxylic acid is represented by the formula R"$CO_2$H wherein R" is an linear or branched alkyl, having from 1 to about 22 carbon atoms.

11. The process according to claim 10 wherein the carboxylic acid is represented by the formula R"$CO_2$H wherein R" is a linear alkyl having from 1 to about 10 carbon atoms.

12. The process according to claim 11 wherein reaction is carried out in a batch reaction in the liquid phase or a continuous flow reactor.

13. A process for producing methyl acetate comprising reacting dimethyl ether and acetic acid in the presence of a catalyst consisting essentially of an iodide of a Group IA element under conditions sufficient to form the methyl acetate and recovering the ester.

14. The process according to claim 13 wherein the catalyst is selected from the group consisting of HI and LiI.

15. The process according to claim 14 wherein the reaction is conducted at a temperature ranging from 125° to about 250° C. and a pressure ranging from 1 atmosphere to about 150 atmospheres.

16. The process according to claim 15 wherein the reaction is carried out in a batch reactor or a continuous flow reactor.

17. The process according to claim 16 wherein the reaction is carried out in the liquid phase in a continuous flow reactor.

* * * * *